United States Patent
Alvarez et al.

(10) Patent No.: US 9,616,156 B2
(45) Date of Patent: Apr. 11, 2017

(54) METHOD, APPARATUS, AND SYSTEM FOR EXPRESSION AND QUANTIFICATION OF HUMAN BREAST MILK

(71) Applicant: Naya Health, Inc., Redwood City, CA (US)

(72) Inventors: Jeffery B. Alvarez, Redwood City, CA (US); Janica B. Alvarez, Redwood City, CA (US); Jan Rydfors, San Mateo, CA (US)

(73) Assignee: Naya Health, Inc., Redwood City, CA (US)

( * ) Notice: Subject to any disclaimer, the term of this patent is extended or adjusted under 35 U.S.C. 154(b) by 401 days.

(21) Appl. No.: 14/221,113

(22) Filed: Mar. 20, 2014

(65) Prior Publication Data

US 2014/0288466 A1    Sep. 25, 2014

Related U.S. Application Data

(60) Provisional application No. 61/804,722, filed on Mar. 24, 2013, provisional application No. 61/879,055, filed on Sep. 17, 2013.

(51) Int. Cl.
*A61M 1/06* (2006.01)
*A61M 1/00* (2006.01)

(52) U.S. Cl.
CPC ............ *A61M 1/06* (2013.01); *A61M 1/0068* (2014.02); *A61M 1/062* (2014.02); *A61M 1/064* (2014.02); *A61M 2205/10* (2013.01)

(58) Field of Classification Search
CPC ........ A61M 1/06; A61M 1/007; A61M 1/062; A61M 1/064; A61M 1/066; A61M 1/068
USPC ...................................... 604/74–76
See application file for complete search history.

(56) References Cited

U.S. PATENT DOCUMENTS

| | | | |
|---|---|---|---|
| 4,263,912 A * | 4/1981 | Adams ................. | A61M 1/066 604/75 |
| 5,007,899 A | 4/1991 | Larsson | |
| 5,423,781 A | 6/1995 | Alexander et al. | |
| 5,885,246 A | 3/1999 | Ford | |
| 6,461,324 B1 * | 10/2002 | Schlensog ............... | A61M 1/06 604/74 |
| 6,616,037 B2 | 9/2003 | Grimm et al. | |

(Continued)

FOREIGN PATENT DOCUMENTS

WO    WO 2012/014135 A1    2/2012

OTHER PUBLICATIONS

International search report and written opinion dated Sep. 2, 2014 for PCT/US2014/031510.

(Continued)

*Primary Examiner* — Rebecca E Eisenberg
(74) *Attorney, Agent, or Firm* — Wilson Sonsini Goodrich & Rosati

(57) ABSTRACT

A device for expression and collection of breast milk includes an actuatable assembly, a breast interface, and a tube. The breast interface is sized to receive a breast and form a fluid tight seal against the breast. The breast interface includes a deformable member disposed within at least a portion of the breast interface. The deformable member deforms in response to actuation of the actuatable assembly and applies vacuum pressure against the breast to express milk. The tube operatively couples the actuatable assembly to the breast interface.

19 Claims, 12 Drawing Sheets

(56) References Cited

U.S. PATENT DOCUMENTS

| | | |
|---|---|---|
| 6,652,484 B1 | 11/2003 | Hunckler et al. |
| 6,673,036 B1 | 1/2004 | Britto |
| 6,749,582 B2 | 6/2004 | Britto et al. |
| 6,840,918 B1 | 1/2005 | Britto et al. |
| 6,887,210 B2 | 5/2005 | Quay |
| 6,997,897 B1 | 2/2006 | Silver et al. |
| 7,029,454 B2 | 4/2006 | Watanabe |
| 7,118,709 B2 | 10/2006 | Treptow |
| 7,662,127 B2 | 2/2010 | Silver et al. |
| 7,758,540 B2 | 7/2010 | Yamashita et al. |
| 7,875,000 B2 | 1/2011 | Krebs et al. |
| 7,887,507 B2 * | 2/2011 | Shemesh ............... A61B 5/411 604/74 |
| 7,972,297 B2 | 7/2011 | Bryan et al. |
| 8,116,933 B2 | 2/2012 | Underdal et al. |
| 8,118,772 B2 | 2/2012 | Dao et al. |
| 8,164,454 B2 | 4/2012 | Teller |
| 8,216,179 B2 | 7/2012 | Bosshard et al. |
| 8,323,235 B2 | 12/2012 | Bryan et al. |
| 8,453,878 B2 | 6/2013 | Palmquist |
| 8,801,658 B2 | 8/2014 | Harari et al. |
| 8,813,551 B2 | 8/2014 | Boiarski |
| 8,827,947 B2 | 9/2014 | Bosman et al. |
| 8,876,760 B2 | 11/2014 | Bosman et al. |
| 9,033,953 B2 | 5/2015 | Felber |
| 2002/0198489 A1 * | 12/2002 | Silver ............... A61M 1/06 604/74 |
| 2003/0153869 A1 | 8/2003 | Ytteborg |
| 2003/0191433 A1 | 10/2003 | Prentiss |
| 2004/0087898 A1 | 5/2004 | Weniger |
| 2005/0043677 A1 | 2/2005 | Kelly et al. |
| 2005/0234370 A1 | 10/2005 | Beal et al. |
| 2006/0042376 A1 | 3/2006 | Reusche et al. |
| 2006/0106334 A1 | 5/2006 | Jordan et al. |
| 2007/0125162 A1 | 6/2007 | Ghazi et al. |
| 2008/0039741 A1 | 2/2008 | Shemesh et al. |
| 2010/0217148 A1 | 8/2010 | Binder |
| 2012/0004603 A1 | 1/2012 | Harari et al. |
| 2012/0316493 A1 | 12/2012 | Schlienger et al. |
| 2012/0325219 A1 | 12/2012 | Smith |
| 2013/0023821 A1 | 1/2013 | Khalil et al. |
| 2013/0096461 A1 | 4/2013 | Sella |
| 2013/0131588 A1 | 5/2013 | Silver et al. |
| 2013/0245548 A1 | 9/2013 | Cook et al. |
| 2014/0121593 A1 * | 5/2014 | Felber ............... A61M 1/06 604/74 |
| 2014/0262918 A1 | 9/2014 | Chu |
| 2014/0263611 A1 | 9/2014 | Bauer |
| 2014/0276629 A1 | 9/2014 | Bauer et al. |
| 2015/0038945 A1 | 2/2015 | McCabe |
| 2015/0051458 A1 | 2/2015 | Chen et al. |
| 2015/0122688 A1 | 5/2015 | Dias et al. |
| 2015/0265753 A1 | 9/2015 | Prentice et al. |
| 2015/0274329 A1 | 10/2015 | Harp et al. |
| 2015/0314053 A1 | 11/2015 | Furrer et al. |
| 2015/0328380 A1 | 11/2015 | Furrer et al. |

OTHER PUBLICATIONS

European Search Report dated Nov. 3, 2016 for EP Application No. 14775743.9.

* cited by examiner

METHOD, APPARATUS, AND SYSTEM FOR EXPRESSION AND QUANTIFICATION OF HUMAN BREAST MILK

CROSS-REFERENCE

The present application is a non-provisional of, and claims the benefit of U.S. Provisional Patent Application Nos. 61/804,722 filed Mar. 24, 2013; and 61/879,055 filed Sep. 17, 2013; the entire contents of which are incorporate herein by reference.

BACKGROUND OF THE INVENTION

1. Field of the Invention

The present invention generally relates to medical devices and methods, and more particularly relates to devices and methods for expression and collection of human breast milk.

The exemplary embodiments disclosed herein are preferably directed at expression of breast milk, but one of skill in the art will appreciate that this is not intended to be limiting and that the devices, systems and methods disclosed herein may be used for other treatments requiring application of a differential pressure.

Breast pumps are commonly used to collect breast milk in order to allow mothers to continue breastfeeding while apart from their children. Currently, there are two primary types of breast pumps: manually-actuated devices, which are small, but inefficient and tiring to use; and electrically-powered devices, which are efficient, but large and bulky. Therefore, it would be desirable to provide improved breast pumps that are small and highly efficient for expression and collection of breast milk. Additional features such as milk production quantification and communication with mobile devices are further desirable for enhanced user convenience. At least some of these objectives will be satisfied by the devices and methods disclosed below.

2. Description of the Background Art

The following U.S. patents are related to expression and collection of human breast milk: U.S. Pat. Nos. 6,673,036; 6,749,582; 6,840,918; 6,887,210; 7,875,000; 8,118,772; and 8,216,179.

SUMMARY OF THE INVENTION

The present invention generally relates to medical devices, systems and methods, and more particularly relates to devices, systems and methods for expression and collection of human breast milk.

In a first aspect of the present invention, a device for expression and collection of breast milk comprises an actuatable assembly, a breast interface, and a tube. The breast interface is sized to engage a breast and fluidly seal thereagainst. The breast interface also includes a movable member disposed within at least a portion thereof. The movable member moves in response to actuation of the actuatable assembly and thereby forms a vacuum in the breast interface and applies the vacuum to the breast to express milk therefrom. The tube is operatively coupled to the actuatable assembly and to the breast interface.

The actuatable assembly may comprise a piston or a pump, or a pair of pistons or a pair of pumps. Actuation of the actuatable assembly may displace a fluid that is disposed in the tube.

The movable member may comprise a flexible membrane. The flexible membrane may have a corrugated region that is configured to expand and collapse. The flexible membrane may deform in response to actuation of the actuatable assembly, and actuation of the actuatable assembly may displace a fluid contained within the tube. The movable member may comprise a deformable member.

The breast interface may comprise a resilient and conformable flange for engaging and creating a fluid seal against the breast.

A fluid may be disposed in the tube. The fluid may be an incompressible fluid such as water or oil. In other embodiments, a tensile element may be disposed in the tube. The tensile element may comprise a rope, a wire, or a cable. The tensile element may be operatively coupled with the movable member and the actuatable assembly, and may also be concentrically disposed with an axial compressive element that absorbs reactive loads of the tensile element.

The device may further comprise a driving mechanism that is operatively coupled with the actuatable assembly, and that is configured to actuate the actuatable assembly. The driving mechanism may include electromechanical device such as a motor. The driving mechanism may be releasably coupled to the actuatable assembly.

The breast interface may comprise an exit valve that is configured to control flow of the expressed breast milk into a collection vessel. The exit valve may control the flow by preventing the expressed milk from flowing through the valve when the deformable member is deformed, and allowing the expressed breast milk to flow through the valve when the deformable member is in an undeformed configuration. The exit valve may be integrally formed into the deformable member.

The device may further comprise a second actuatable assembly, a second breast interface and a second tube. The second breast interface may be sized to engage a second breast and fluidly seal thereagainst. The second breast interface may have a movable member disposed within at least a portion thereof, and the movable member may deform in response to actuation by either the actuatable assembly or the optional second actuatable assembly and thereby form a vacuum in the second breast interface which is applied to the second breast to express milk therefrom. The second tube may be operatively coupled to the second actuatable assembly and the second breast interface.

The device may further comprise a housing having a controller for controlling actuation of the actuatable assembly. The controller may control calculation and display of breast milk production information, and the controller may also control communication with other devices. A power source may be disposed in the housing and the power source provides power to the device for expression and collection of milk. The housing may have a drive mechanism disposed therein for actuating the actuatable assembly.

The device may further comprise a collection vessel fluidly coupled with the breast interface. The device may also comprise a sensor adjacent the breast interface, and that is configured to measure an aspect of mil passage therepast. The device may also comprise a display unit for displaying data related to the expression of the milk. A system for expression and collection of breast milk may include the device previously described above. Any of these components may be separate from the other components or they may be disposed in a housing or pendant.

In another aspect of the present invention, a device for applying pressure or vacuum to a patient comprises an actuatable assembly, a target tissue interface, and a tube. The target tissue interface is preferably sized to engage a target tissue and fluidly seal thereagainst. The target tissue interface has a deformable member disposed within at least a portion thereof, and the deformable member deforms in response to actuation of the actuatable assembly. This forms a vacuum or pressure in the target tissue interface and applies the vacuum or the pressure to the target tissue. The tube is operatively coupled to the actuatable assembly and the target tissue interface.

In yet another aspect of the present invention, a method for expressing and collecting breast milk comprises providing a breast expression and collection device having a breast interface and an actuatable assembly operatively coupled to the breast interface. The breast interface comprises a deformable member. The method also comprises engaging and fluidly sealing a breast with the breast interface and actuating the actuatable assembly. The method also comprises deforming the deformable member in response to actuation of the actuatable assembly thereby creating and applying a vacuum to the breast, and expressing and collecting milk from the breast.

The engaging step may comprise engaging a resilient and conformable flange on the breast interface with the breast thereby creating a fluid seal between the breast interface and the breast.

Actuating the actuatable assembly may displace a fluid. The fluid may be disposed in a tube that is fluidly coupled with the actuatable assembly and the deformable member. Actuating the actuatable assembly may comprise moving a piston or applying a tension to a tensile element disposed in the tube. The method may further comprise releasing the actuatable assembly from a driving mechanism that is operatively coupled therewith.

The method may further comprise repeating the actuating, the deforming and the expressing steps. The method may further comprise quantifying production of the expressed milk and transmitting data related to the expression of breast milk between the breast expression and collection device and a mobile device. The mobile device may be a smart phone, tablet, or computing device. The data may be displayed on a display. The method may also comprise controlling flow of the expressed milk into a collection vessel with a valve fluidly coupled to the breast expression and collection device. Controlling the flow may comprise opening the valve when the deformable member is undeformed, and closing the valve when the deformable member is deformed. Aspects of breast milk may also be sensed with a sensor that may be fluidly or otherwise coupled with the breast interface.

The breast expression and collection device may further comprise a second breast interface and a second actuatable assembly operatively coupled to the second breast interface. The second breast interface may comprise a deformable member. The method may further comprise engaging and fluidly sealing a second breast with the second breast interface, and actuating the first or the second actuatable assembly. The method may also comprise deforming the deformable member in the second breast interface in response to actuation of the second actuatable assembly thereby creating and applying a vacuum to the second breast, and expressing and collecting milk from the second breast. Expressing and collecting milk from both breasts may occur simultaneously or it may alternate between both breasts.

In still another aspect of the present invention, a method of applying a differential pressure to a patient comprises providing a differential pressure device having an interface and an actuatable assembly operatively coupled to the differential pressure device. The interface comprises a deformable member and the method further comprises engaging and fluidly sealing the interface with a target region on the patient, and actuating the actuatable assembly. The method also comprises deforming the deformable member in response to actuation of the actuatable assembly thereby creating a positive pressure or a vacuum and applying the positive pressure or the vacuum to the target region. Any of the components may be separate from the other components, or they may be diposed in a housing or pendant.

Deforming the deformable member may create a positive pressure that is applied to the target region. The target region may comprise the mouth or nose, and applying the positive pressure reduces or eliminates apnea or similar disorders while the patient is sleeping. Deforming the flexible membrane may create a vacuum that is applied to the target region. The target region may comprise a body fluid reservoir, and thus the vacuum causes expression of a body fluid from the reservoir.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed devices and methods will now be described with reference to the drawings. Nothing in this detailed description is intended to imply that any particular component, feature, or step is essential to the invention. One of skill in the art will appreciate that various features or steps may be substituted or combined with one another.

The present invention will be described in relation to the expression and collection of breast milk. However, one of skill in the art will appreciate that this is not intended to be limiting, and the devices and methods disclosed herein may be used in other applications involving the creation and transmission of a pressure differential, such as in the treatment of sleep apnea and/or other remote pressure needs.

Figure 1:
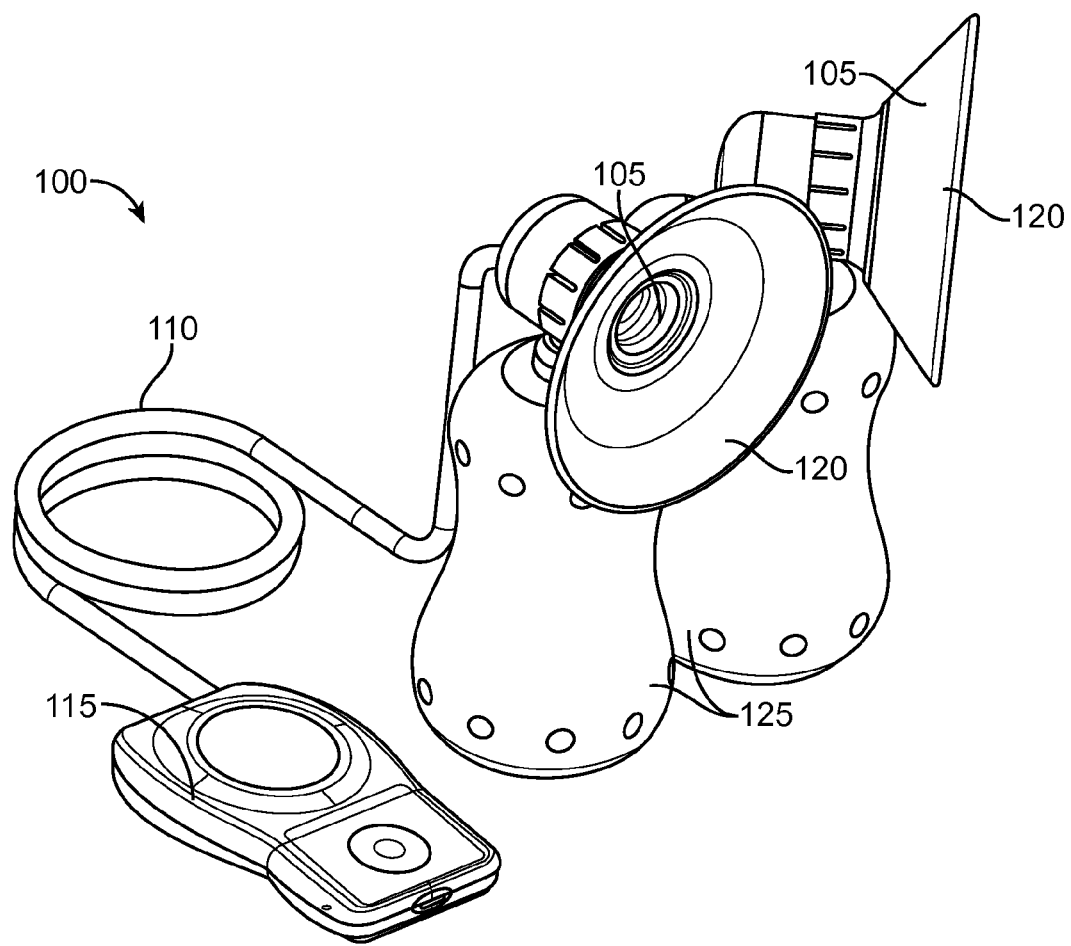
FIG. 1 is a perspective view of an exemplary embodiment of a pumping device.

FIG. 1 illustrates an exemplary embodiment of the present invention. Pumping device 100 includes breast interfaces 105, a tube 110, and a controller or pendant unit 115 operatively coupled to breast interfaces 105 through tube 110. Breast interfaces 105 include resilient and conformable flanges 120, for engaging and creating a fluid seal against the breasts, and collection vessels 125. The device may optionally only have a single breast interface. Pendant unit 115 houses the power source and drive mechanism for pumping device 100, and also contains hardware for various functions, such as controlling pumping device 100, milk production quantification, and communication with other devices. Tube 110 transmits suitable energy inputs, such as mechanical energy inputs, from pendant unit 115 over a long distance to breast interfaces 105. Breast interfaces 105 convert the energy inputs into vacuum pressure against the breasts in a highly efficient manner, resulting in the expression of milk into collection vessels 125.

One of skill in the art will appreciate that components and features of this exemplary embodiment can be combined or substituted with components and features of any of the embodiments of the present invention as described below. Similarly, components and features of other embodiments disclosed herein may be substituted or combined with one another.

Hydraulic Pumping Device

Hydraulic systems can reduce pumping force requirements, and therefore also reduce the size of the pumping device, while maintaining high pumping efficiency. In a preferred embodiment, the pumping device can utilize a hydraulic pumping device to generate a pressure differential against the breast for the expression and collection of milk.

Figure 2:
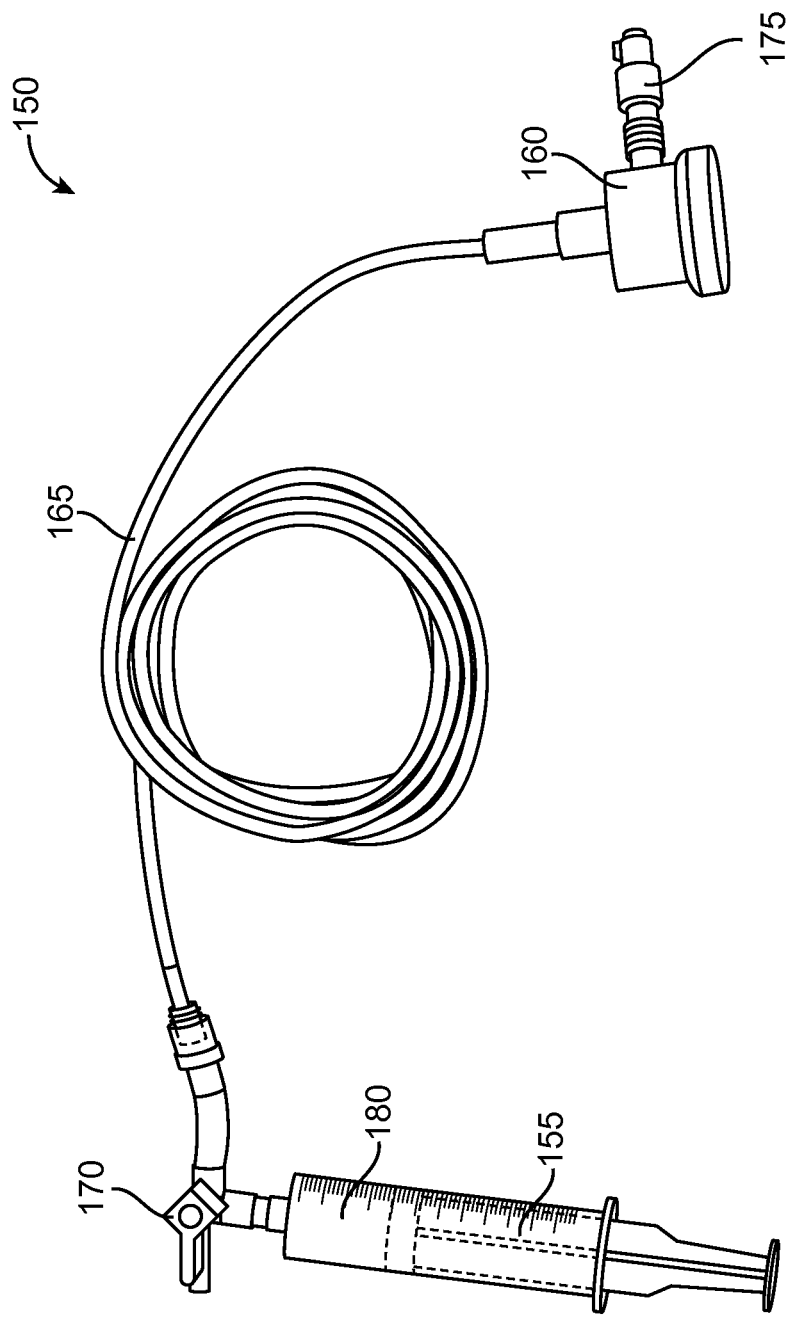
FIG. 2 is a perspective view of an exemplary embodiment of a pumping device.
Figure 3:
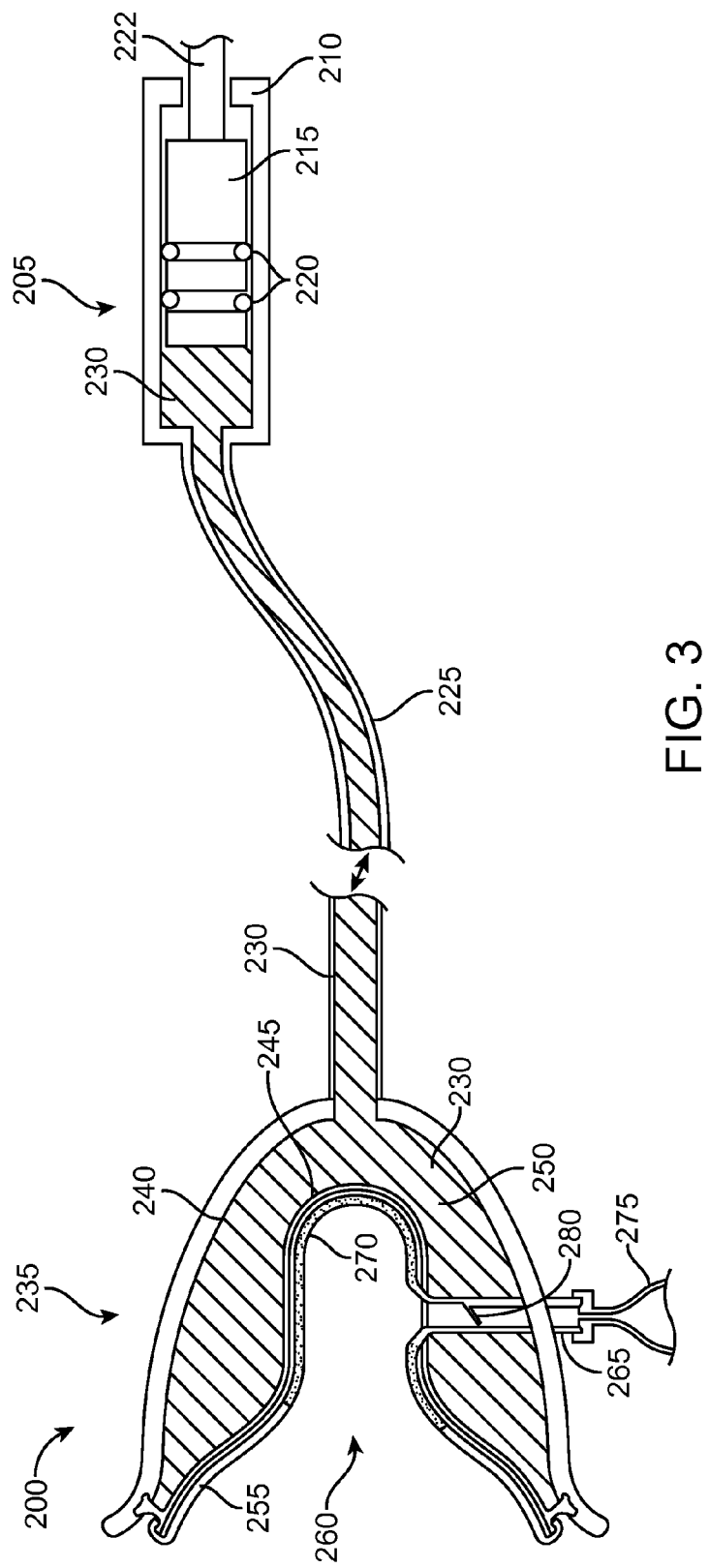
FIG. 3 is a cross-section of an exemplary embodiment of a pumping device.

Exemplary hydraulic pumping devices are depicted in FIGS. 2 and 3. FIG. 2 illustrates a pumping device 150 with a syringe 155 fluidly coupled to breast interface 160 by tube 165. Syringe 155 is coupled to tube 165 through a three-way valve 170. Breast interface 160 contains an exit port 175. The syringe 155 drives a fluid 180 contained within tube 165 against or away from a flexible member contained within breast interface 160 to create the pressure differential necessary for milk expression from the breast.

FIG. 3 illustrates another embodiment of a pumping device 200. The actuatable assembly 205 includes an assembly housing 210, a driving element 215, radial seals 220, and a shaft 222. Driving element 215 is operatively coupled to a pendant unit, such as pendant unit 115, through shaft 222. The tube 225 contains a fluid 230 and is fluidly coupled to the actuatable assembly 205 and the breast interface 235. The breast interface 235 consists of an interface housing 240, a flexible membrane 245, a reservoir 250, a sealing element 255, an expression area 260, and a drain port 265. The sealing element 255 includes deformable portion 270. The drain port 265 is coupled to a collection vessel 275 and includes a flap valve 280.

Actuatable assembly 205 displaces fluid 230 contained within tube 225, which can be a flexible line. Fluid 230 occupies reservoir 250 within breast interface 235 and is coupled with flexible membrane 245. Flexible membrane 245 transmits vacuum pressure from fluid 230 to the deformable portion 270 of sealing element 255. When a breast is engaged into and fluidly sealed with breast interface 235 by sealing element 255, displacement of the actuatable element 215 produces substantial vacuum pressure against the breast through flexible membrane 245 and deformable portion 270, resulting in the expression of breast milk into expression area 260. The expressed milk drains through drain port 265 into collection vessel 275. Drain port 265 is configured with a flap valve 280 to provide passage of milk while maintaining vacuum pressure in expression area 260.

The fluid for the hydraulic pumping device can be any suitable fluid, such as an incompressible fluid. In many embodiments, the incompressible fluid can be water or oil. Alternatively, the fluid can be any suitable gas, such as air. Suitable incompressible fluids and gases for hydraulic systems are known to those of skill in the art.

One of skill in the art will appreciate that components and features of any of the exemplary embodiments of the hydraulic pumping device can be combined or substituted with components and features of any of the embodiments of the present invention as described herein.

Actuation Mechanism

Many actuation mechanisms known to those of skill in the art can be utilized for the actuatable assembly 205. Actuatable assembly 205 can be a piston assembly, a pump such as a diaphragm pump, or any other suitable actuation mechanism. The optimal configuration for actuatable assembly 205 can depend on a number of factors, such as: vacuum requirements; size, power, and other needs of the pumping device 200; and the properties of the fluid 230, such as viscosity, biocompatibility, and fluid life requirements.

FIG. 3 illustrates an exemplary embodiment in which actuatable assembly 205 is a piston assembly and driving element 215 is a piston. Actuatable assembly 205 includes radial seals 220, such as O-rings, sealing against assembly housing 210 to prevent undesired egress of fluid 230 and to enable driving of fluid 230.

Figure 4:
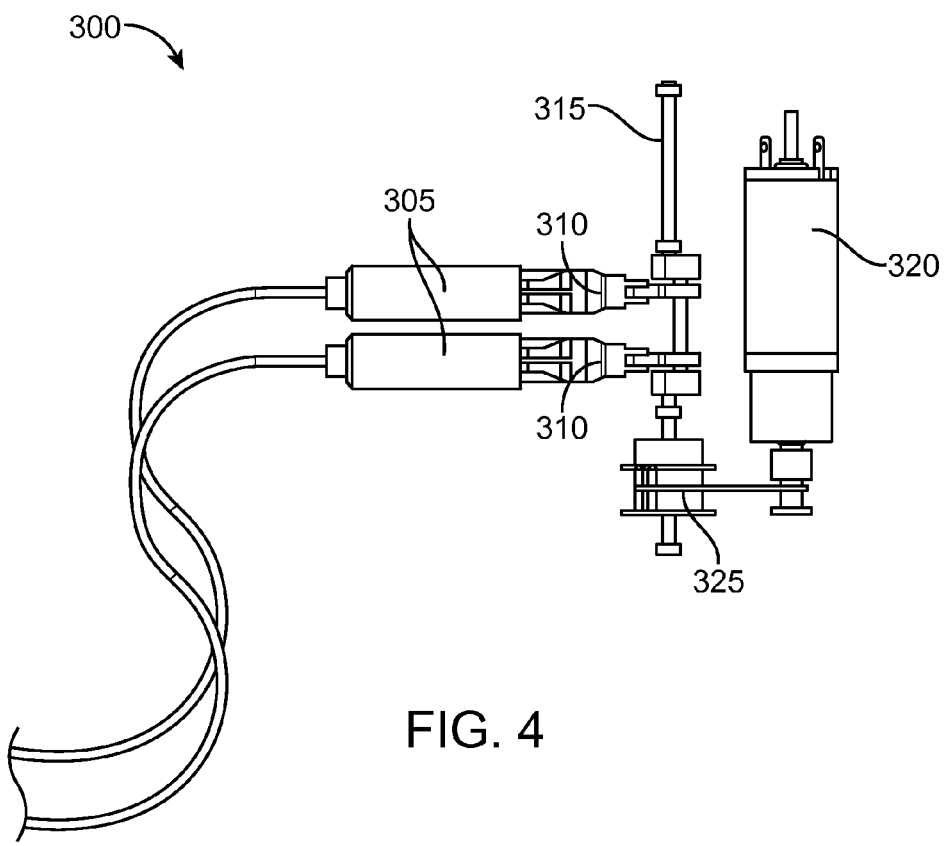
FIG. 4 illustrates an exemplary embodiment of an actuatable assembly coupled to a driving mechanism.

FIG. 4 illustrates another exemplary embodiment of an actuatable assembly 300 including a pair of pistons 305.

In preferred embodiments, the actuatable assembly includes a driving element powered by a suitable driving mechanism, such as a driving mechanism residing in pendant unit 115. Many driving mechanisms are known to those of skill in the art. For instance, the driving element, such as driving element 215, may be actuated electromechanically by a motor, or manually by a suitable user-operated interface, such as a lever. Various drive modalities known to those of skill in the art can be used. In particular, implementation of the exemplary hydraulic pumping devices as described herein enables the use of suitable drive modalities such as direct drive and solenoids, owing to the reduced force requirements of hydraulic systems.

Referring now to the exemplary embodiment of FIG. 4, the pistons 305 include couplings 310 to a crankshaft 315. The crankshaft 315 is operatively coupled to a motor 320 through a belt drive 325. The crankshaft 315 drives the pair of pistons 305 with the same stroke timing in order to apply vacuum pressure against both breasts simultaneously, a feature desirable for increased milk production. Alternatively, the crankshaft 315 can drive the pair of pistons 305 with any suitable stroke timing, such as alternating or offset stroke cycles.

The driving mechanism can be powered by any suitable power source, such as a local battery or an AC adaptor. The driving mechanism can be controlled by hardware, such as onboard electronics located within pendant unit 115.

Figure 5A:
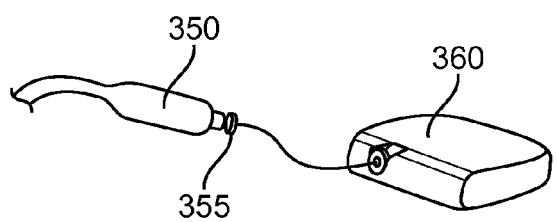
FIGS. 5A-5B illustrate an exemplary embodiment of an actuatable assembly coupled to a pendant unit.
Figure 5B:
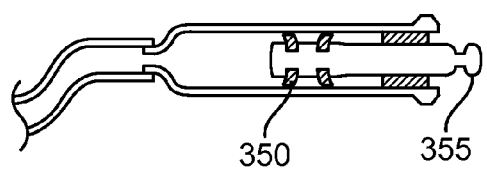

FIG. 5 illustrates an exemplary embodiment of an actuatable assembly 350 that includes releasable coupling 355. Preferably, actuatable assembly 350 is releasably coupled to a pendant unit 360 and the driving mechanism housed therein. The coupling can be a mechanical coupling or any suitable quick release mechanism known to those of skill in the art. The releasably coupled design allows for flexibility in the configuration and use of the pumping device. For instance, user comfort can be improved through the use of differently sized breast interfaces for compatibility with various breast sizes. Additionally, this feature enables a common pumping device to be used with interchangeable breast interfaces, thus reducing the risk of spreading pathogens. Furthermore, the releasable coupling enables easy replacement of individual parts of the pumping device.

One of skill in the art will appreciate that components and features of any of the exemplary embodiments of the actuation mechanism can be combined or substituted with components and features of any of the embodiments of the present invention as described herein.

Flexible Membrane

In many embodiments such as the embodiment depicted in FIG. 3, the flexible membrane 245 is located within breast interface 235 and disposed over at least portion thereof, forming reservoir 250 between the interface housing 240 and the flexible membrane 245. Preferably, the flexible membrane 245 deforms substantially when subject to the negative pressures created when the fluid 230 is displaced from reservoir 250 by actuatable assembly 205. The amount of deformation of the flexible membrane 245 can be controlled by many factors, (e.g., wall thickness, durometer, surface area) and can be optimized based on the pumping device (e.g., pump power, vacuum requirements).

Figure 6:
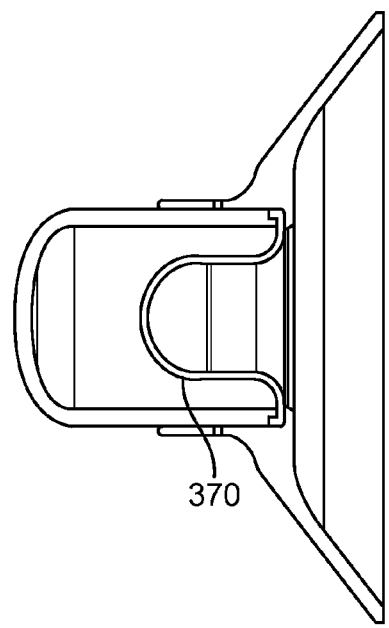
FIG. 6 is a cross-sectional view of an exemplary embodiment of a breast interface.

FIG. 6 illustrates an exemplary flexible membrane 370 with a specified thickness and durometer.

Figure 7:
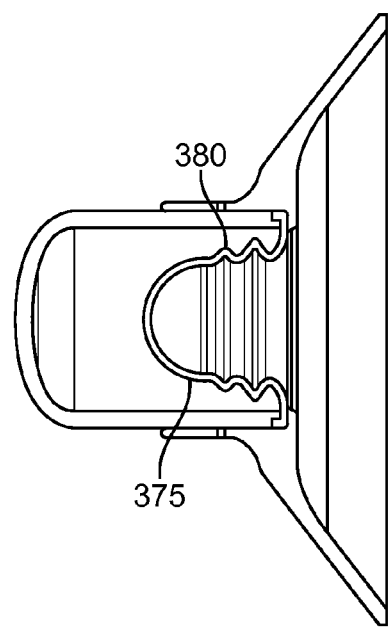
FIG. 7 is a cross-sectional view of another exemplary embodiment of a breast interface.

FIG. 7 illustrates another embodiment of flexible membrane 375 with corrugated features 380 for increased surface area.

Suitable materials for the flexible membrane are known to those of skill in the art. In many embodiments, the flexible membrane can be made of a material designed to expand and contract when subject to pressures from the coupling fluid such as silicone, polyether block amides such as PEBAX, and polychloroprenes such as neoprene. Alternatively, the flexible membrane can be fabricated from a substantially rigid material, such as stainless steel, nitinol, high durometer polymer, or high durometer elastomer. In these embodiments, the rigid material would be designed with stress and/or strain distribution elements to enable the substantial deformation of the flexible membrane without surpassing the yield point of the material.

Figure 8A:
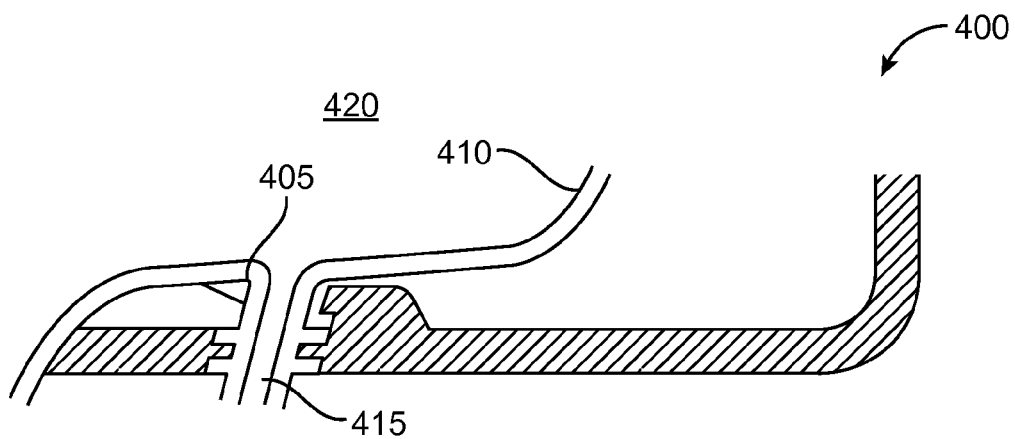
FIG. 8A is a cross-sectional view of an exemplary embodiment of an integrated valve in an open position.
Figure 8B:
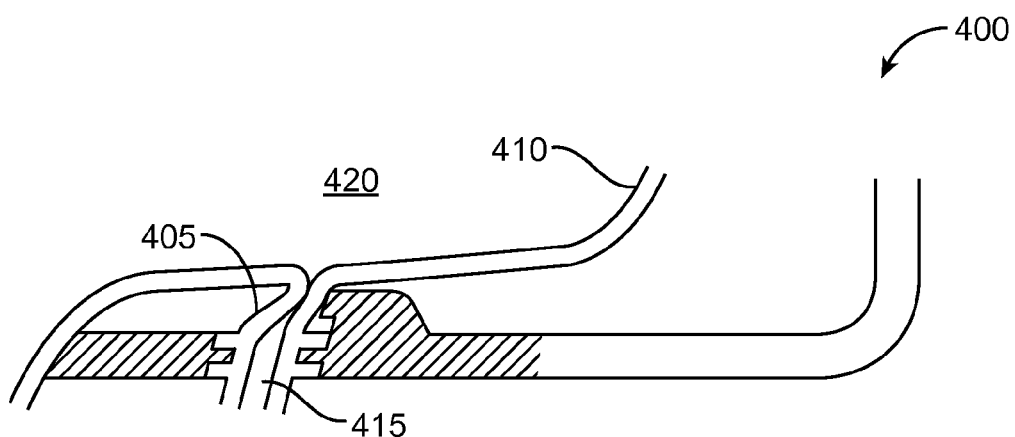
FIG. 8B is a cross-sectional view of an exemplary embodiment of an integrated valve in a closed position.

FIGS. 8A and 8B illustrate preferred embodiments of a breast interface 400 in which an exit valve 405 is integrated into the flexible membrane 410 to control the flow of expressed milk through exit port 415. The exit valve 405 is opened to allow fluid flow when the flexible membrane 410 is relaxed, as shown in FIG. 8A, and is closed to prevent fluid flow when the flexible membrane 410 is deformed, as shown in FIG. 8B. The exit valve 405 enables substantial vacuum pressure to be present in expression area 420 during extraction, while allowing milk to drain during the rest phase of the pump stroke. While many conventional breast pump valves function on pressure differentials alone, the exit valve 405 can preferably be configured to also function on the mechanical movement of flexible membrane 410. Incorporation of an integrated exit valve 405 with mechanical functionality as described herein can improve the sealing of the breast interface 400 during vacuum creation. Furthermore, the implementation of an exit valve integrally formed within the flexible membrane 410 such as exit valve 405 reduces the number of parts to be cleaned.

One of skill in the art will appreciate that components and features of any of the exemplary embodiments of the flexible membrane can be combined or substituted with components and features of any of the embodiments of the present invention as described herein.

Milk Collection and Quantification System

With reference to FIG. 3, expressed milk drains through exit port 265 in flexible membrane 245 into a collection vessel 275. Collection vessel 275 can be any suitable container, such as a bottle or a bag. In many embodiments, collection vessel 275 is removably coupled to flexible membrane 245. Collection vessel 275 can be coupled directly or remotely via any suitable device such as extension tubing.

In many instances, it can be desirable to track various data related to milk expression and collection, such as the amount of milk production. Currently, the tracking of milk production is commonly accomplished by manual measurements and record-keeping. Exemplary embodiments of the device described herein may provide digital-based means to automatically measure and track milk production for improved convenience, efficiency, and accuracy.

Figure 9A:
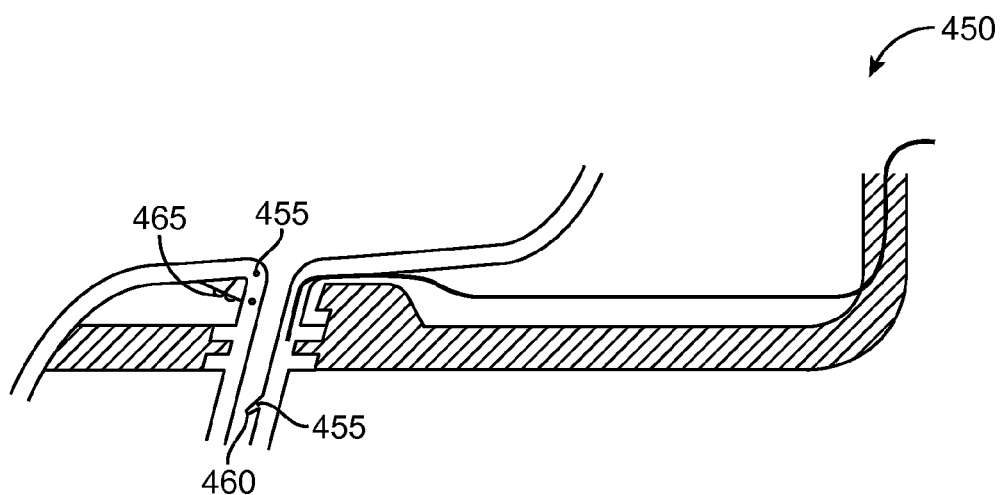
FIG. 9A is a cross-sectional view of an exemplary embodiment of integrated sensors within a breast interface.
Figure 9B:
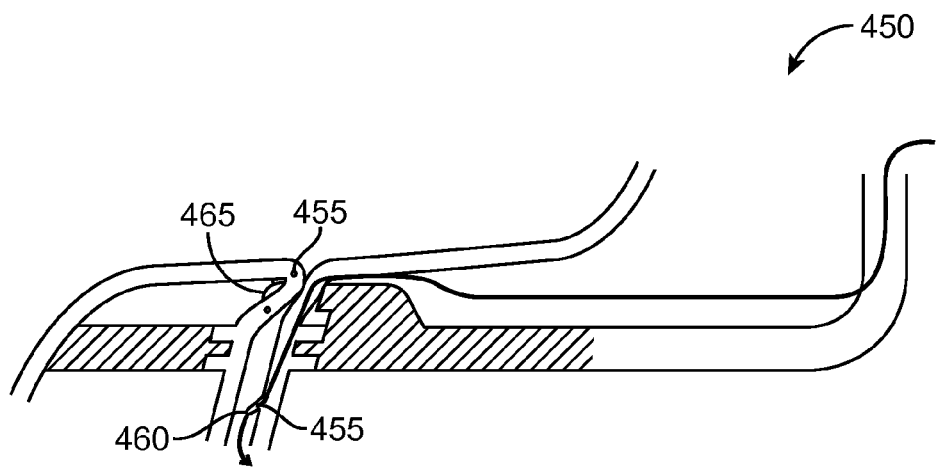
FIG. 9B is a cross-sectional view of another exemplary embodiment of integrated sensors within a breast interface.

FIGS. 9A and 9B illustrates exemplary embodiments of a breast interface 450 with one or more integrated sensors 455. Sensors 455 are preferably located in flap valve 460, but may also be located in exit valve 465, or any other suitable location for monitoring fluid flow. In a preferred embodiment, at least one sensor 455 is integrated into a valve that is opened by fluid flow and detects the length of time that the valve is opened. The sensor signal can be interrogated to quantify the fluid flow. Suitable sensors are known to those of skill in the art, such as accelerometers, Hall effect sensors, and photodiode/LED sensors. The breast interface can include a single sensor or multiple sensors to quantify milk production.

Figure 10:
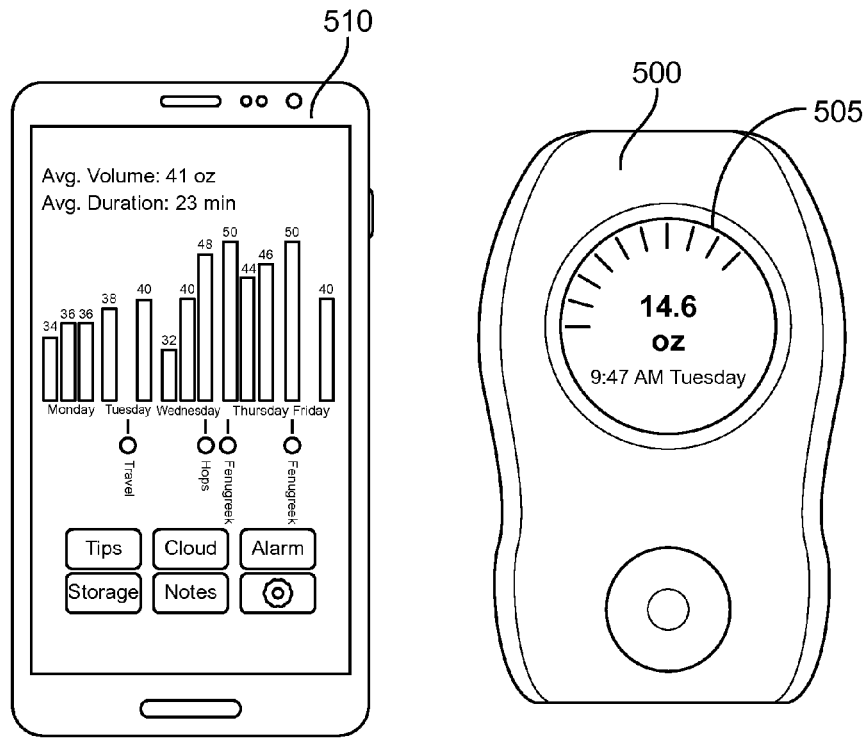
FIG. 10 illustrates an exemplary embodiment of a pendant unit and a mobile device.

FIG. 10 illustrates an exemplary embodiment of pendant unit 500 in which milk expression data is shown on a display screen 505. In many embodiments, the pendant unit 500 collects, processes, stores, and displays data related to milk expression. Preferably, the pendant unit 500 can transmit the data to a second device, such as a mobile phone 510.

Figure 11:
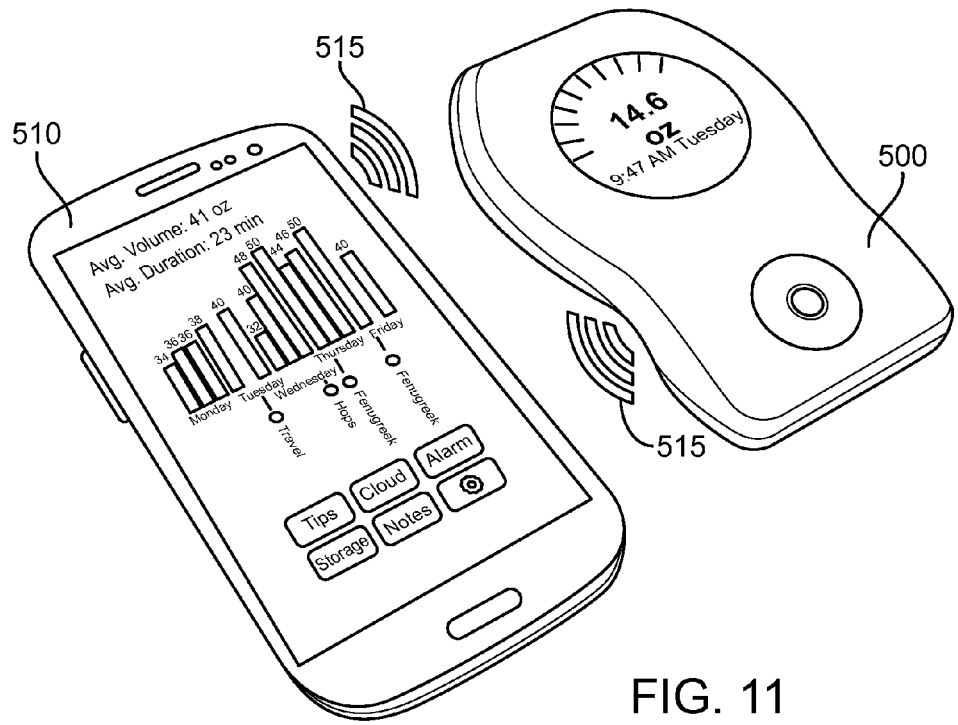
FIG. 11 illustrates an exemplary embodiment of a pendant unit in communication with a mobile device.

FIG. 11 illustrates data transmission 515 between pendant unit 500 and a mobile phone 510. Suitable methods for communication and data transmission between devices are known to those of skill in the art, such as Bluetooth or near field communication.

In exemplary embodiments, the pendant unit 500 communicates with a mobile phone 510 to transmit milk expression data, such as expression volume, duration, and date. The mobile phone 510 includes a mobile application to collect and aggregate the expression data and display it in an interactive format. Preferably, the mobile application includes additional features that allow the user to overlay information such as lifestyle choices, diet, and strategies for increasing milk production, in order to facilitate the comparison of such information with milk production statistics. Additionally, the pendant unit 500 can send information about the times of pump usage to the mobile phone 510 so that the mobile application can identify when pumping has occurred and set reminders at desired pumping times. Such reminders can help avoid missed pumping sessions, and thus reduce the incidence of associated complications such as mastitis.

One of skill in the art will appreciate that components and features of any of the exemplary embodiments of the milk collection and quantification system can be combined or substituted with components and features of any of the embodiments of the present invention as described herein.

Mechanical Pumping Device

Figure 12:
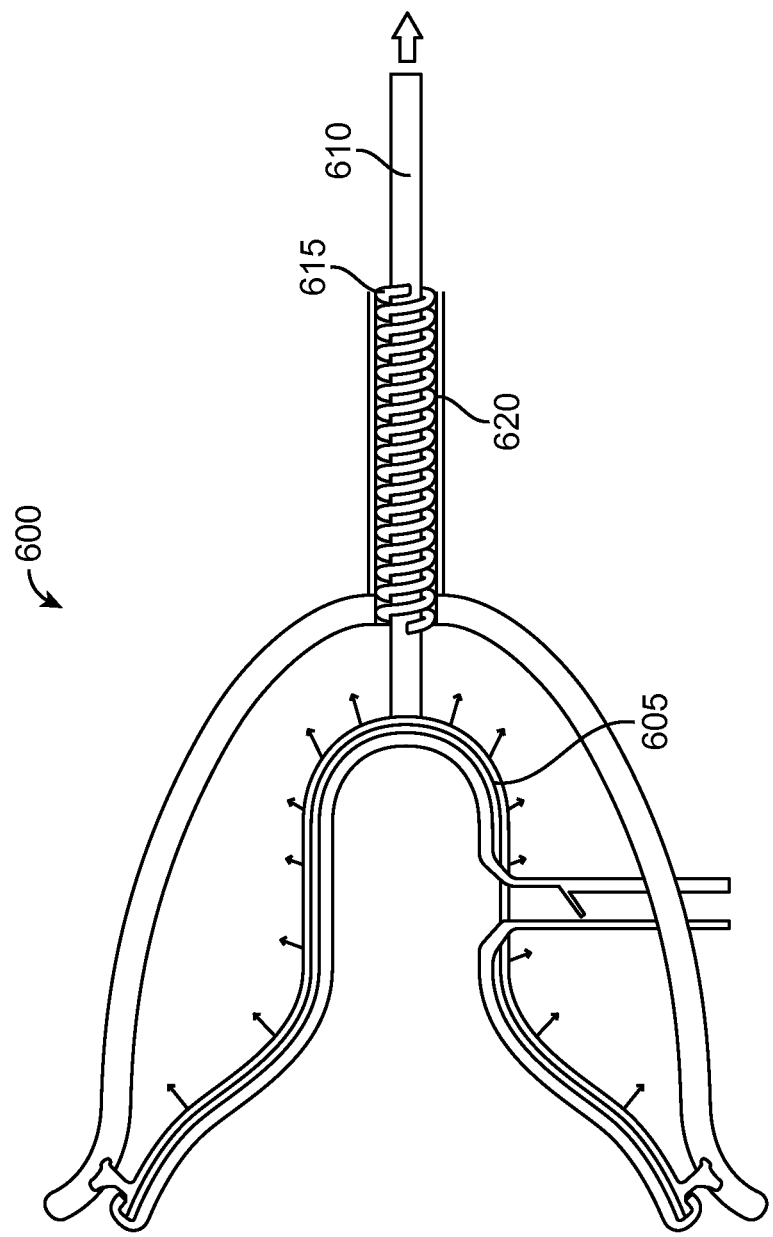
FIG. 12 is a cross-sectional view of an exemplary embodiment of a breast interface with a mechanical deformable member.

FIG. 12 illustrates an alternative embodiment of a breast interface 600 in which a mechanical deformable member 605 can be used in place of a flexible membrane. The mechanical deformable member 605 can be constructed from similar techniques as those used for the flexible membrane as described herein. The mechanical deformable member 605 is coupled to a tensile element 610. In some instances, tensile element 610 is disposed within an axial load absorbing member 615. The axial load absorbing member 615 is disposed within tube 620. Preferably, tensile element 610 is concentrically disposed within axial load absorbing member 615 and axial load absorbing member 615 is concentrically disposed within tube 620. Alternative arrangements of tensile element 610, axial load absorbing member 615, and tube 620 can also be used.

Figure 13:
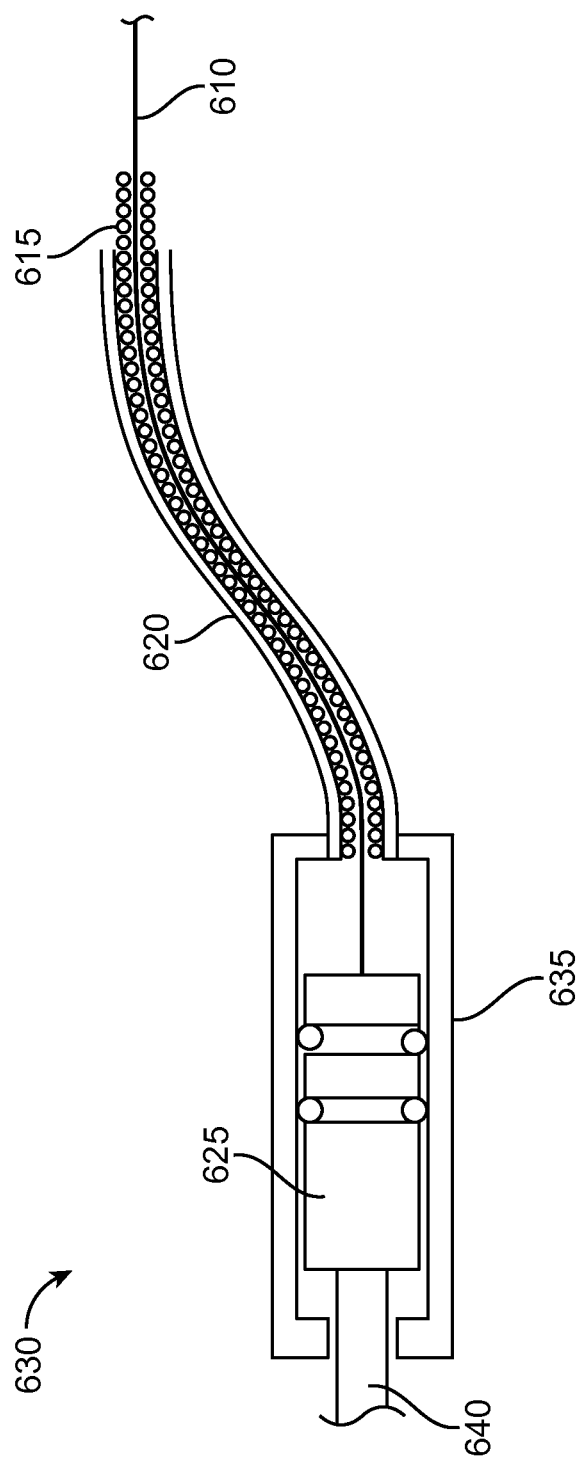
FIG. 13 is a cross-sectional view of an exemplary embodiment of a mechanical driver for a mechanical deformable member.

FIG. 13 illustrates the tensile element 610 coupled to driving element 625 of an actuatable assembly 630 within an assembly housing 635. Driving element 625 is operatively coupled to a driving mechanism, such as a driving mechanism housed within a pendant unit, through shaft 640. Axial load absorbing member 615 within tube 620 is fixedly coupled to the assembly housing 635. Displacement of the driving element 625 transmits tensile force through tensile element 610 to the mechanical deforming member 605 to create vacuum pressure against the breast.

The tensile element 610 can be any suitable device, such as a wire, coil, or rope, and can be made from any suitable material, such as metals, polymers, or elastomers. Axial load absorbing member 615 can be made from any suitable axially stiff materials, such as metals or polymers, and can be configured into any suitable axially stiff geometry, such as a tube or coil.

One of skill in the art will appreciate that components and features of any of the exemplary embodiments of the mechanical pumping device can be combined or substituted with components and features of any of the embodiments of the present invention as described herein.

Experimental Data

Figure 14:
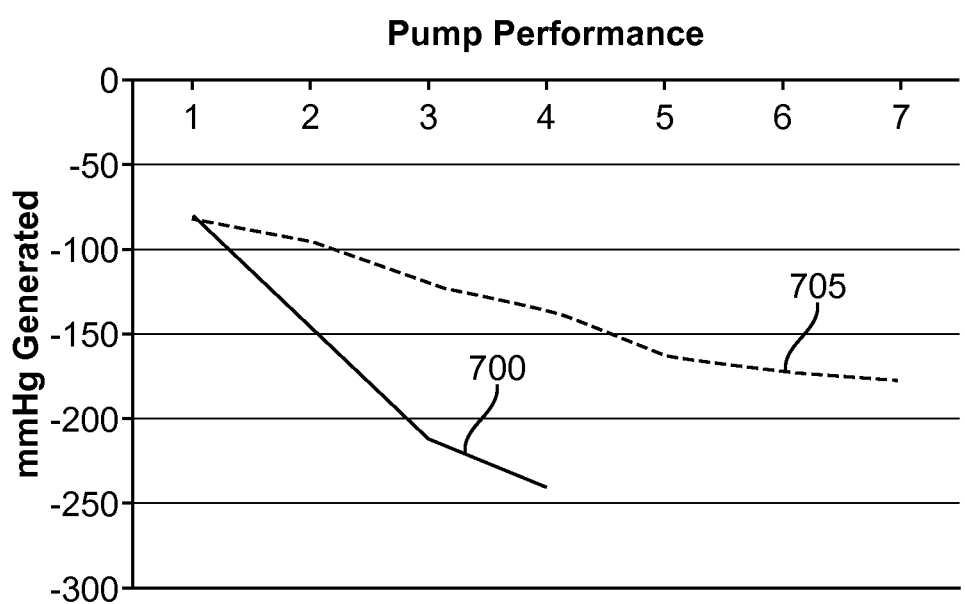
FIG. 14 is a graph illustrating the pump performance of an exemplary embodiment compared to a commercial device.
Figure 15:
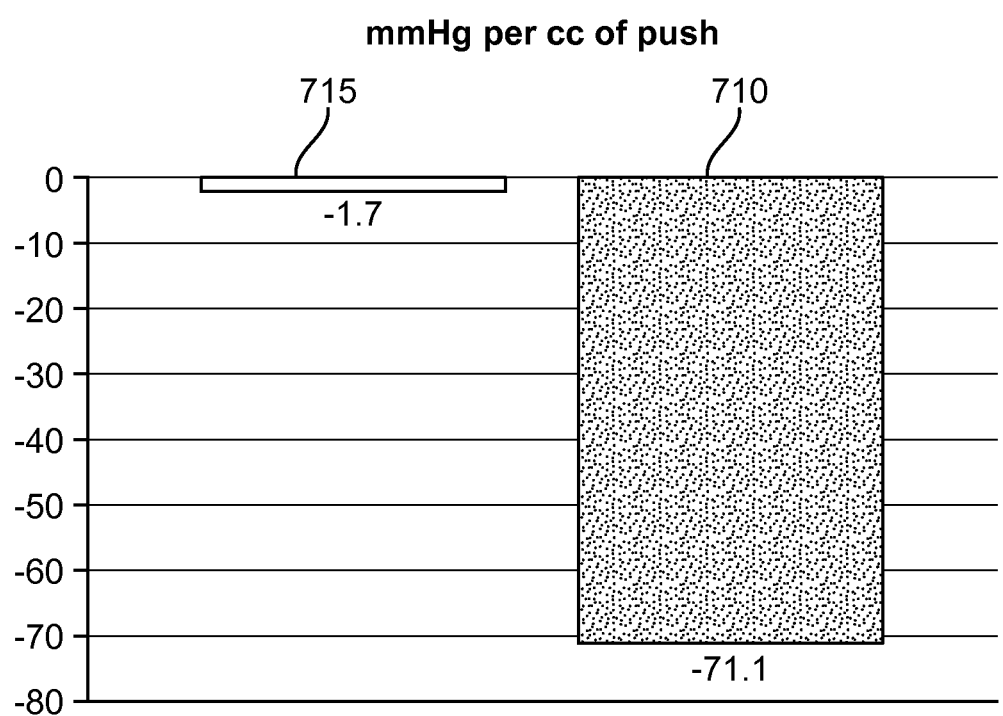
FIG. 15 is a graph illustrating the pumping efficiency of an exemplary embodiment compared to a commercial device.

FIGS. 14 and 15 illustrate experimental pumping data obtained from a commercial breast pump device and an exemplary embodiment of the present invention. The exemplary embodiment utilized an incompressible fluid for pumping and had a maximum hydraulic fluid volume of 4 cc, while the commercial device utilized air for pumping and had a maximum volume of 114 cc.

FIG. 14 illustrates a graph of the pump performance as quantified by vacuum pressure generated per run. For the exemplary embodiment, pressure measurements were taken for 1 cc, 2 cc, 3 cc, and 4 cc of fluid volume displaced by the pump, with the run number corresponding to the volume in cc. For the commercial device, measurements were taken with the pump set to one of seven equally incremented positions along the vacuum adjustment gauge representing 46 cc, 57 cc, 68 cc, 80 cc, 91 cc, 103 cc, and 114 cc of fluid volume displaced by the pump, respectively, with the run number corresponding to the position number. Curve 700 corresponds to the exemplary embodiment and curve 705 corresponds to the commercial device. The exemplary embodiment generated higher levels of vacuum pressure per displacement volume compared to the commercial device, with maximum vacuum pressures of −240.5 mmHg and −177.9 mmHg, respectively.

FIG. 15 illustrates a graph of the pump efficiency as measured by the maximum vacuum pressure per maximum volume of fluid displaced, with bar 710 corresponding to the exemplary embodiment and bar 715 corresponding to the commercial device. The exemplary embodiment demonstrated a 42-fold increase in pumping efficiency compared to the commercial device, with efficiencies of −71.1 mmHg/cc and −1.7 mmHg/cc, respectively.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for expression and collection of breast milk, said device comprising:
   an actuatable assembly;
   a breast interface configured to engage a breast and fluidly seal thereagainst, the breast interface comprising a housing and a single, continuous membrane disposed within and coupled to the housing to form a continuous reservoir therebetween, the reservoir comprising a sole negative pressure source for the breast interface, the reservoir extending between the housing and the membrane and filled with an incompressible liquid so as to be fluidly separated from the breast milk expressed from the breast, wherein the membrane is shaped to form a first opening configured to receive at least a nipple of the breast therethrough; and
   a tube operatively coupling the actuatable assembly to the breast interface,
   wherein the actuatable assembly, when actuated, is configured to affect movement of at least a portion of the liquid out of the reservoir, and
   wherein the membrane is configured to move away from the nipple in response to movement of the liquid out of the reservoir, thereby generating sufficient negative pressure with the sole negative pressure source at the breast interface to cause expression of the breast milk from the breast.

2. The device of claim 1, wherein the actuatable assembly comprises a piston or a pump.

3. The device of claim 1, wherein the tube is filled with the liquid, and wherein the actuatable assembly is configured to displace the liquid disposed in the tube when actuated.

4. The device of claim 1, wherein the membrane is flexible.

5. The device of claim 1, wherein the membrane is configured to move circumferentially about the nipple in response to movement of the liquid out of the reservoir.

6. The device of claim 1, wherein the membrane comprises a deformable portion.

7. The device of claim 1, wherein the reservoir is configured to be disposed circumferentially about the nipple.

8. The device of claim 1, further comprising an electromechanical driving mechanism operatively coupled with the actuatable assembly, and configured to actuate the actuatable assembly.

9. The device of claim 1, wherein the membrane is further shaped to form a second opening to allow the breast milk to exit the breast interface therethrough, the second opening smaller than the first opening.

10. The device of claim 9, wherein first opening is directed laterally to receive the breast therethrough, and wherein the second opening is directed downwards to allow the breast milk to drain therethrough by gravity.

11. The device of claim 1, wherein the breast interface comprises an exit valve, the exit valve configured to control flow of the expressed breast milk out of the breast interface into a collection vessel.

12. The device of claim 11, wherein the membrane is shaped to form the exit valve.

13. The device of claim 1, further comprising a controller for controlling actuation of the actuatable assembly, controlling calculation and display of breast milk production information, or controlling communication with other devices.

14. The device of claim 1, further comprising a sensor adjacent the breast interface, the sensor configured to sense at least one aspect of milk flowing therepast.

15. A method of expressing and collecting breast milk, said method comprising:
   providing a breast expression and collection device having a breast interface and an actuatable assembly operatively coupled thereto, wherein the breast interface comprises a single, continuous membrane disposed within and coupled to a housing to form a continuous reservoir therebetween, the reservoir comprising a sole negative pressure source for the breast interface;
   engaging and fluidly sealing a breast with the breast interface such that at least a nipple of the breast is received through a first opening of the membrane;
   actuating the actuatable assembly;
   moving at least a portion of an incompressible liquid disposed within the reservoir out of the reservoir in response to actuation of the actuatable assembly;
   moving the membrane away from the nipple in response to movement of the liquid out of the reservoir, thereby creating and applying sufficient negative pressure with the sole negative pressure source at the breast interface to cause expression of the breast milk from the breast; and
   expressing and collecting the breast milk from the breast.

16. The method of claim 15, wherein actuating the actuatable assembly displaces the liquid disposed within a tube that operatively couples the actuatable assembly and the breast interface, thereby moving the liquid out of the reservoir.

17. The method of claim 15, wherein moving the membrane away from the nipple comprises moving the membrane circumferentially about the nipple.

18. The method of claim 15, wherein actuating the actuatable assembly comprises moving a piston.

19. The method of claim 15, further comprising sensing at least one aspect of the expressed breast milk with a sensor fluidly coupled with the breast interface.

* * * * *